United States Patent
Berner

(10) Patent No.: US 10,040,727 B2
(45) Date of Patent: Aug. 7, 2018

(54) PROCESS FOR PROVIDING A DEFINED SURFACE TOPOGRAPHY TO AT LEAST A PORTION OF A CERAMIC BODY

(71) Applicant: STRAUMANN HOLDING AG, Basel (CH)

(72) Inventor: Simon Berner, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 4 days.

(21) Appl. No.: 15/106,863

(22) PCT Filed: Dec. 22, 2014

(86) PCT No.: PCT/EP2014/079024
§ 371 (c)(1),
(2) Date: Jun. 21, 2016

(87) PCT Pub. No.: WO2015/097167
PCT Pub. Date: Jul. 2, 2015

(65) Prior Publication Data
US 2017/0001920 A1 Jan. 5, 2017

(30) Foreign Application Priority Data

Dec. 23, 2013 (GB) .................................. 1322907.5

(51) Int. Cl.
| | |
|---|---|
| C04B 41/53 | (2006.01) |
| A61C 8/00 | (2006.01) |
| C04B 41/00 | (2006.01) |
| C04B 41/87 | (2006.01) |
| C04B 41/50 | (2006.01) |
| C04B 111/00 | (2006.01) |

(52) U.S. Cl.
CPC .......... *C04B 41/5353* (2013.01); *A61C 8/005* (2013.01); *A61C 8/0012* (2013.01); *A61C 8/0013* (2013.01); *C04B 41/009* (2013.01); *C04B 41/5042* (2013.01); *C04B 41/87* (2013.01); *A61C 2008/0046* (2013.01); *C04B 2111/00836* (2013.01)

(58) Field of Classification Search
None
See application file for complete search history.

(56) References Cited

U.S. PATENT DOCUMENTS

| | | | | |
|---|---|---|---|---|
| 5,866,271 A | * | 2/1999 | Stueber .................... | C23C 28/00 148/240 |
| 8,110,242 B2 | * | 2/2012 | Hawkins .................. | A61L 27/28 427/2.1 |
| 2004/0267376 A1 | * | 12/2004 | Suzuki ..................... | A61L 27/10 623/23.5 |
| 2008/0213726 A1 | * | 9/2008 | Schlottig ................. | A61L 27/10 433/201.1 |
| 2012/0021008 A1 | * | 1/2012 | De Bruijn ............... | A61K 33/42 424/400 |
| 2012/0189833 A1 | * | 7/2012 | Suchanek ................. | C01F 7/34 428/219 |
| 2014/0141201 A1 | * | 5/2014 | Berner ..................... | A61L 27/30 428/141 |

FOREIGN PATENT DOCUMENTS

| | | |
|---|---|---|
| EP | 1 982 670 A1 | 10/2008 |
| WO | 2012/175218 A1 | 12/2012 |
| WO | 2014/101997 A1 | 7/2014 |
| WO | 2014/101998 A1 | 7/2014 |

OTHER PUBLICATIONS

Mar. 6, 2015 International Search Report issued in International Patent Application No. PCT/EP2014/079024.
Jul. 30, 2014 Search Report issued in British Patent Application No. 1322907.5.
Jul. 7, 2016 International Preliminary Report on Patentability issued in International Patent Application No. PCT/EP2014/079024.

* cited by examiner

Primary Examiner — Shamim Ahmed
(74) Attorney, Agent, or Firm — Oliff PLC

(57) ABSTRACT

A Process for providing a defined surface topography to at least a portion of a ceramic body, the process comprising the subsequent steps of
a) applying a layer of a calcium containing substance comprising at least one calcium compound onto the surface of at least a portion of the ceramic basic body;
b) thermally treating the ceramic basic body with the layer applied thereon at an elevated temperature, whereby a calcium compound or a calcium component based on the calcium compound diffuses into the basic body to form an intermediate body, said intermediate body comprising in its outermost surface region a calcium containing crystalline phase; and
c) chemically treating the outermost surface region of the intermediate body with an inorganic acid or base to partially remove the calcium containing crystalline phase, thereby obtaining the surface topography.

12 Claims, 12 Drawing Sheets

Figure 1A:
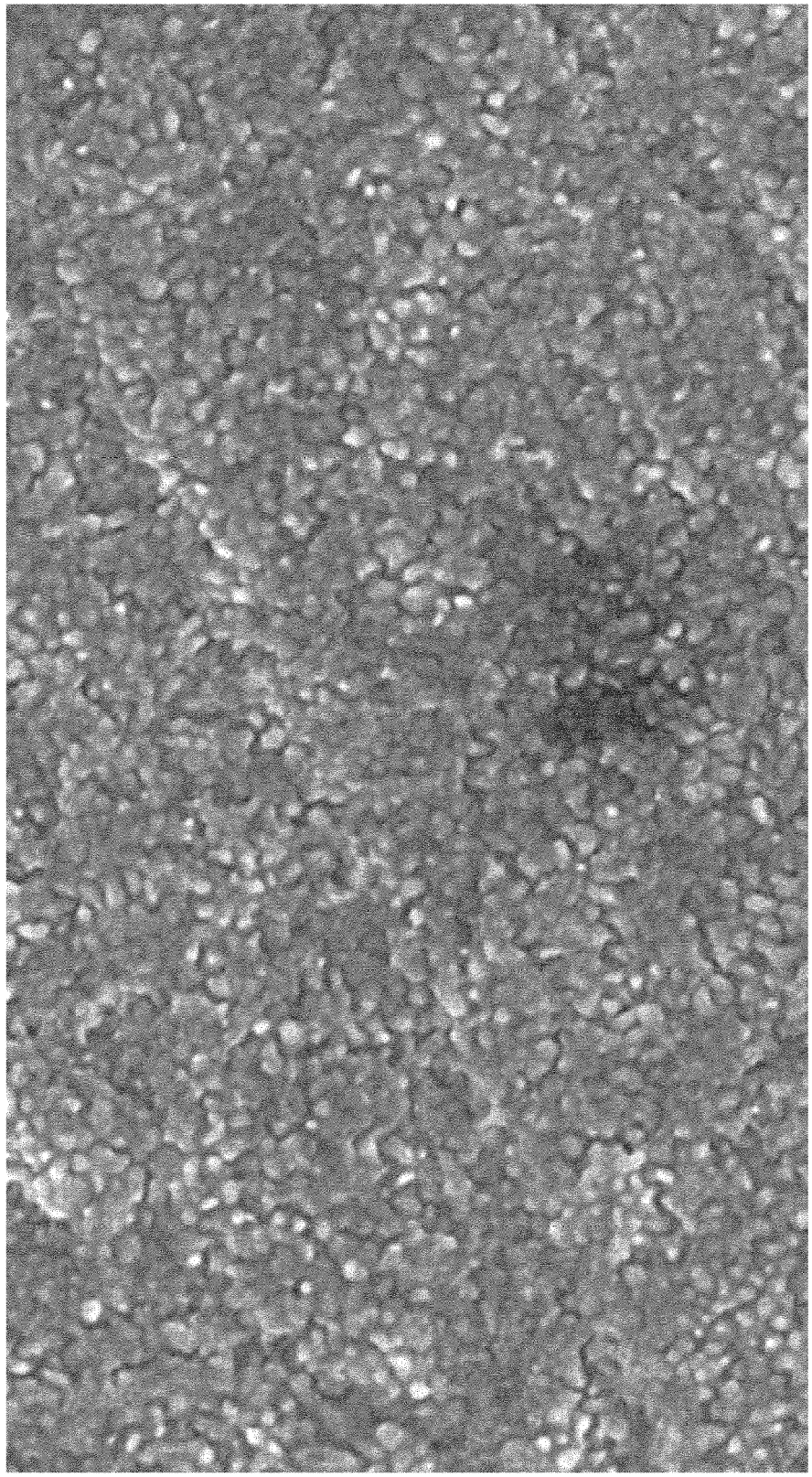
Figure 1B:
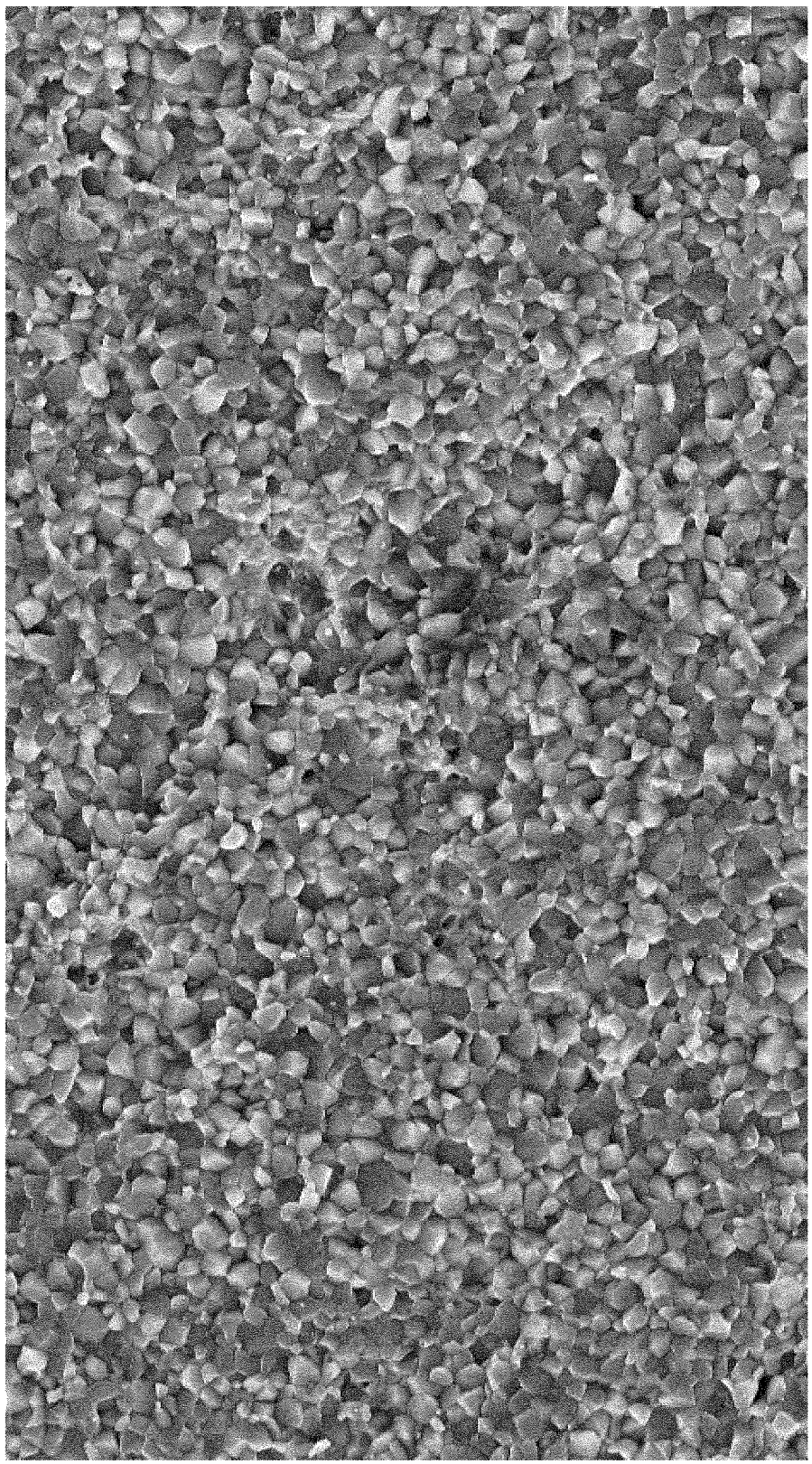

PROCESS FOR PROVIDING A DEFINED SURFACE TOPOGRAPHY TO AT LEAST A PORTION OF A CERAMIC BODY

The present invention relates to a process for providing a defined surface topography to at least a portion of a ceramic body. The invention further relates to a ceramic body, at least a portion of which having a surface topography that is at least partially formed of a roughness-providing ceramic material, as well as to the use of the ceramic body as an implant, in particular a dental implant, or an abutment.

Dental implants are well known in the art. They generally consist of a material, which is biocompatible and which additionally has a high mechanical strength allowing long-term success rates of the implant when exposed to appropriate biomechanical loads.

The major part of the dental implants currently used consists of titanium. Titanium meets the above mentioned requirements, i.e. it is biocompatible and has a relatively high mechanical strength with a sufficiently low elastic modulus. In addition, titanium implants allow a favourable interaction with the surrounding tissue, i.e. bone tissue and soft tissue, to be achieved.

The direct structural and functional connection between living bone and the surface of the load-bearing implant is referred to in the art as "osseointegration" (or "osteointegration"). A good osseointegration means that the implant, after reaching a primary stability by screwing it into the bone, safely ossifies within a short healing time so that a permanent bond between implant and bone is obtained.

For titanium implants, a breakthrough technology in the development of highly osseointegrative surfaces is the so-called "SLA" process, involving sandblasting the implant's surface followed by acid-etching to achieve an optimal topography for the attachment of bone cells. In this context it is referred to EP-A-0 388 576, which describes the treatment of a titanium implant by a blasting process using corundum, and subsequent etching with a reducing acid, such as HF, HCl or HCl with $H_2SO_4$.

From an aesthetic point of view, titanium has, however, the disadvantage that it is dark in color and therefore mismatches with the natural tooth color.

In contrast to titanium, the color of ceramic materials can be closely matched to the natural tooth color.

Efforts have thus been made to provide dental implants of which at least the parts that are visible after insertion are made of a ceramic material.

A ceramic material having a sufficiently high mechanical strength is disclosed in U.S. Pat. No. 6,165,925, which relates to an yttrium-stabilized zirconia in predominantly tetragonal form for the production of a sintered semi-finished article as a starting material for the manufacture of a prosthesis.

In order to achieve a sufficient mechanical strength, the zirconia ceramic disclosed in U.S. Pat. No. 6,165,925 must be highly dense.

Although the behavior of a ceramic material towards bone tissue and soft tissue is different compared to the respective behavior of a metallic material, such as titanium, efforts have been made to provide a surface topography also on a ceramic dental implant in order to achieve improved osteointegrative properties. This has turned out to be a difficult task, since the surface of the zirconia ceramic described in U.S. Pat. No. 6,165,925 is clean cut, extremely hard and has essentially no porosity.

A solution for providing osteointegrative properties to the surface of a ceramic material, such as the one disclosed in U.S. Pat. No. 6,165,925, is disclosed in EP-A-1 982 670, according to which the surface of the dental implant is etched with an etching solution comprising hydrofluoric acid at a temperature of at least 70° C.

Despite the favourable osteointegrative properties achieved by this process, it involves the handling of hydrofluoric acid, which is highly corrosive and a contact poison, and should thus be handled with extreme care, going beyond that of other inorganic acids. Also, the process requires hydrofluoric acid to be used at relatively harsh conditions, namely at a temperature of above 70° C. The safety measures that have to be taken when carrying out the process according to EP-A-1 982 670 are, thus, relatively elaborate.

In consideration of this, the problem to be solved by the present invention is to provide a relatively simple, yet safe process for providing a defined surface topography to a ceramic body, particularly to a ceramic implant, more particularly to a ceramic dental implant, or a ceramic abutment.

A further problem to be solved by the present invention is to provide a ceramic body, particularly an implant, more particularly a dental implant, or an abutment, said body having a high mechanical strength and allowing for a good interaction with the surrounding tissue, specifically the bone tissue or the soft tissue, respectively.

The problem is solved by the process according to claim 1 and the ceramic body according to claims 11 and 12, respectively. Preferred embodiments of the invention are given in the dependent claims.

According to claim 1, the invention, thus, relates to a process for providing a defined surface topography to at least a portion of a ceramic body, the process comprising the subsequent steps of
   a) applying a layer of a calcium containing substance comprising at least one calcium compound onto the surface of at least a portion of the ceramic basic body;
   b) thermally treating the ceramic basic body with the layer applied thereon at an elevated temperature, whereby a calcium compound or a calcium component based on the calcium compound diffuses into the basic body to form an intermediate body, said intermediate body comprising in its outermost surface region a calcium containing crystalline phase; and
   c) chemically treating the outermost surface region of the intermediate body with an inorganic acid or base to partially remove the calcium containing crystalline phase, thereby obtaining the surface topography.

It has surprisingly been found that a ceramic material comprising a calcium containing crystalline phase can be etched by an inorganic acid or base other than hydrofluoric acid. In other words, the ceramic material containing the calcium containing crystalline phase functions as a "roughness-providing ceramic material" in that it is selectively and partially etched such as to leave a rough surface on the ceramic body.

By way of forming an intermediate body comprising in its outermost surface region a calcium containing crystalline phase, the present invention, thus, allows a defined surface topography, in particular a rough surface topography, to be prepared by an etching procedure that is both simple and safe. In particular, the process of the present invention can be carried out without complying with strict safety requirements, as is the case when using an etching solution comprising hydrofluoric acid.

Contrary to the technologies described in the state of the art that either propose a subtractive treatment, such as the one suggested by EP-A-1 982 670, or an additive treatment, such as the one suggested by EP-A-2 496 167, the process of the present invention combines additive process steps, namely of applying a substance comprising a specific compound onto the surface of a ceramic basic body and letting the compound or a component based on the compound diffuse into the basic body by a thermal treatment, with a subtractive process step, namely the chemical treatment with an inorganic acid or base.

With regard to the thermal treatment, the amount of calcium compound or calcium component to diffuse into the basic body is chosen such that in its outermost surface region the calcium containing crystalline phase is formed.

Calcium is thereby integrated into the material in a continuous material formation. This is in clear difference to a basic body with a calcium coating applied thereon, whereby a discrete interface between the basic body and the coating is formed.

In this regard, it is further to be noted that the term "calcium containing crystalline phase" as used in the context of the present invention is to be understood as a crystalline phase in which calcium is arranged periodically, meaning that it occupies a defined position within the crystal lattice system. This is in contrast to a crystalline material in which calcium is present as a mere stabilizing agent, i.e. an agent that serves to stabilize the crystal structure of a given phase, but which is not arranged periodically within the crystal lattice system.

Preferably, the ceramic basic body is made of yttria-stabilized zirconia. By using yttria-stabilized zirconia, a body having a particularly high mechanical strength can be achieved.

In this regard, the term "yttria-stabilized zirconia" encompasses—besides purely yttria-stabilized zirconia—any yttria-stabilized zirconia that is co-stabilized with a co-stabilizing agent, such as cerium and/or magnesium or their respective oxides.

Also, the term "yttria-stabilized zirconia" encompasses both a material based on zirconia particles co-precipitated with yttria as well as a material based on yttria-coated zirconia particles.

An example of an yttria-stabilized zirconia based on zirconia particles co-precipitated with yttria is $ZrO_2$-TZP/TZP-A Bio-HIP® ($ZrO_2$) Bioceramic of Metoxit AG, Switzerland. The composition of this ceramic material comprises 92.1 to 93.5 weight-% $ZrO_2$, 4.5 to 5.5 weight-% $Y_2O_3$, 1.8 to 2.2 weight-% $HfO_2$ and 0.25 weight-% $Al_2O_3$. It offers a particularly high mechanical stability and strength, in particular when prepared by hot isostatic pressing or by sintering with subsequent hot isostatic densification. A detailed description of the ceramic material is given in U.S. Pat. No. 6,165,925, the disclosure of which is incorporated herein in its entirety by reference.

Apart from yttria-stabilized zirconia, also e.g. ceria-stabilized or magnesia-stabilized zirconia as well as zirconia stabilized with strontium, ytterbium, gadolinium or neodymium or their oxides, respectively, are thinkable and also encompassed by the term "ceramic material" according to the present invention.

As mentioned, the calcium containing crystalline phase is formed by letting the calcium compound or calcium component to diffuse into the basic body.

According to a further preferred embodiment, the calcium containing crystalline phase is a Ca—Zr—O phase, i.e. a phase, the crystal structure of which contains calcium, zirconium and oxygen only. It is especially preferred that the calcium containing crystalline phase is a $CaO$—$ZrO_2$ phase (also referred to as calcium zirconate phase), and more preferably is selected from the group consisting of a monoclinic $CaZr_4O_9$ phase, a cubic $CaZrO_3$ phase and an orthorhombic $CaZrO_3$ phase. It is thereby particularly preferred that the calcium containing crystalline phase is an orthorhombic $CaZrO_3$ phase. Other calcium containing crystalline phases of particular interest include $Ca(ZrO_3)$, $Ca_{0.2}Zr_{0.8}O_{0.8}$, and $CaZr_4O_9$.

With regard to step a) of the process of the present invention, the calcium containing substance can be any substance suitable for the application of the calcium compound onto the surface of the basic body. The term "calcium containing substance" encompasses in particular a substance essentially consisting of the calcium compound as well as substances comprising besides the calcium compound at least one further component. According to a particularly preferred embodiment, the calcium containing substance is a calcium containing gel or a calcium containing slurry and/or dispersion.

The calcium compound contained in the calcium containing substance is preferably selected from the group consisting of a calcium salt, calcium oxide, calcium hydroxide, metallic calcium, and mixtures thereof, and preferably is selected from the group consisting of $CaO$, $CaCO_3$, $Ca(HCO_3)_2$, $Ca(NO_3)_2$ and mixtures thereof. Specifically, the term "calcium salt" thereby includes those salts comprising an anion that is instable, e.g. against temperature, water, air, etc., like e.g. $Ca(HCO_3)_2$.

The application of the calcium containing substance can be carried out by e.g. soaking/immersion, dipping or drop casting into a respective suspension or emulsion, by a sol-gel-process, by embedding into powder, e.g. when using $CaCO_3$, by spin coating, electrophoresis, sandblasting, chemical vapour deposition, physical vapour deposition, atomic layer deposition and/or ion implantation, in particular by plasma immersion ion implantation (PIII).

It has been found that by applying a sol-gel-process or a process using a slurry and/or dispersion, a particularly high amount of calcium or calcium oxide diffusing into the body can be achieved.

With regard to step b), it is further preferred that the thermal treatment is carried out at a temperature of at least 500° C., preferably at least 800° C., more preferably at least 900° C. The specific temperature is dependent on the ceramic material of the basic body, the specific calcium compound applied as well as the depth of diffusion to be achieved. It is typically above the decomposition temperature of the respective calcium compound.

Likewise, also the duration of the thermal treatment depends on the ceramic material of the basic body, the calcium compound used and the depth of diffusion to be achieved, and a skilled person, who has come aware of the present invention, knows how to set these parameters in order to obtain the results to be achieved.

The basic body is typically prepared by a sintering process. Sintering processes for achieving a ceramic body, and in particular a ceramic dental implant, are well known to a skilled person.

It is in this regard thinkable that step a), i.e. the application of the calcium containing substance, is performed on the (pre-sintered) white body, which is afterwards subjected to the final sintering temperature and thus simultaneously also to the thermal treatment according to step b). This process is particularly suitable if a great depth of diffusion is to be achieved.

The calcium compound or calcium component diffusing into the basic body is typically calcium or calcium oxide (calcia), but can be any other calcium compound or calcium component able to diffuse into the basic body by the thermal treatment.

The diffusion of the calcium compound or calcium component together with a stabilizing agent, specifically yttrium (or yttria), is particularly preferred. It is thus particularly preferred that in addition to the calcium containing substance a stabilizing agent, specifically yttrium and/or yttria, is applied onto the surface of the basic ceramic body, said stabilizing agent co-diffusing into the basic ceramic body by the thermal treatment.

In this context, the calcium containing substance and the stabilizing agent can be applied in two separate steps or simultaneously.

If they are applied in two separate steps, the stabilizing agent can either be applied before or after applying the calcium containing substance.

Further, they can be applied by different methods of application. For example, the stabilizing agent, specifically yttrium, can be applied by physical vapour deposition, followed by the application of the calcium containing substance by soaking/immersion into a respective suspension.

It is further possible to apply either one of the calcium containing substance and the stabilizing agent in a first step, followed by a first thermal treatment in order to let the calcium compound or component or the stabilizing agent, respectively, diffuse into the ceramic basic body in a second step, then apply the other one of the calcium containing substance and the stabilizing agent, i.e. the one not applied in the first step, in a third step, followed by a second thermal treatment in order to let the calcium compound or component or the stabilizing agent, respectively, diffuse into the ceramic basic body in a fourth step. In this regard, the temperature of the first thermal treatment and the temperature of the second thermal treatment can be different.

Most surprisingly, it has been found that by using yttrium (or yttria) in addition to the calcium containing substance, the calcium compound or calcium component, specifically calcium or calcia, diffuses deeper into the ceramic material than if no yttrium/yttria is co-diffused.

It has been found that besides calcium or calcia, also e.g. magnesium, silicon, titanium, aluminium, indium, lanthanum and/or scandium as well as their respective oxides can be integrated into the ceramic material by diffusion using a thermal treatment in analogy to the one described above.

With regard to step c), the inorganic acid or base used for the chemical treatment is preferably selected from the group consisting of $HNO_3$, $HCl$, $HF$, $H_3PO_4$, $H_2SO_4$ and $NaOH$, and mixtures thereof. The etching is thereby performed such that the calcium containing crystalline phase is removed only partially, such as to leave the desired surface topography on the ceramic body.

As will be discussed by way of the figures, the concentration of the inorganic acid or base, respectively, is chosen depending on the specific surface topography to be achieved and can be readily adapted by a person skilled in the art who has become aware of the present invention.

As also shown by the figures, it is particularly preferred that the inorganic acid is selected from the group consisting of $HCl$, $H_3PO_4$ and $H_2SO_4$ as well as mixtures thereof, and most preferably is $H_3PO_4$. The inorganic base can in particular be $NaOH$.

According to a further preferred embodiment, HF can be used for the chemical treatment according to step c). In contrast to the harsh conditions used in the process according to EP-A-1 982 670, relatively mild conditions can be used for achieving partial removal of the calcium containing crystalline phase. In particular, very low concentrations of HF have been found to be sufficient for partial removal of the calcium containing crystalline phase, as will be shown by way of the specific working examples. Specifically, HF diluted in water in a volume ratio of $H_2O$ to HF of at least 4:1, preferably at least 16:1 and most preferably at least 80:1, has been found to be sufficient for the purposes of the present invention. Thus, the concentration of HF can be chosen such that only the calcium containing crystalline phase is partially removed, while leaving the integrity of ceramic material of the body, specifically yttria-stabilized zirconia, unaffected.

According to a further preferred embodiment, the process of the present invention further comprises the step of roughening at least a part of the surface of the basic body by a subtractive mechanical treatment, preferably sand-blasting. This subtractive mechanical treatment is preferably carried out before step a) of the present invention. More preferably, it is applied after at least one sintering step for preparing the ceramic basic body, specifically on the pre-sintered white body or after the final sintering step.

In other words, the process according to this embodiment comprises a subtractive treatment step, specifically of sand-blasting the surface, followed by an additive treatment step, namely of applying a substance comprising a calcium containing compound onto the surface of a ceramic basic body and letting the calcium compound or a component based thereon diffuse into the basic body by a thermal treatment, said additive treatment step then again being followed by a further subtractive treatment step, namely the chemical treatment with an inorganic acid or base.

By the subtractive mechanical treatment, and in particular the sand-blasting, a "macrostructure" is obtained, which is then modulated by the "microstructure" obtained by the chemical treatment.

Ultimately, a surface topography is thereby achieved which allows for a particularly good interaction with the surrounding tissue, and specifically the bone tissue.

In more concrete terms, it is preferred that the surface topography to be provided by the process of the present invention is defined by the arithmetic mean height Sa (3D roughness parameter) being in a range from 0.1 µm and 1.7 µm, preferably being in a range from 0.3 µm to 0.9 µm, more preferably from 0.4 µm to 0.75 µm, and most preferably from 0.6 µm to 0.75 µm. Methods for determining Sa are well known to the skilled person; an exemplary description of its determination is further given below.

It has been found that for a ceramic body, a particularly strong interaction with the surrounding tissue, specifically the bone tissue, can be achieved.

Preferably, the surface topography is further defined by the skewness of the height distribution $S_{sk}$ (3D roughness parameter) being in a range from −0.6 to 0.6, preferably from −0.4 to 0.6, more preferably from −0.3 to 0.5. Methods for determining $S_{sk}$ are well known to the skilled person; an exemplary description of its determination is further given below.

Preferably, the surface topography is further defined by a developed surface area Sdr being in a range from 5% to 40%, preferably in a range from 10% to 30%. Sdr is measured in % enlargement compared to a totally plane reference area which equals to the measured area. Sdr is in the art also referred to as interfacial area and methods for its determination are well known to the skilled person.

As mentioned, the determination of surface topography parameters is well known to the skilled person.

According to one specific example, measurement is carried out using a confocal microscope (μsurf explorer, NanoFocus AG, Oberhausen, Germany) with the following specifications:
   Light source: green LED (wavelength 505 nm);
   Scan mode: piezoelectric scanner, 0.07 μm interval between subsequent images of the image stack;
   Object lens: 20× (working distance 3.1 mm, numerical aperture 0.45);
   Field of view: 798 μm×798 μm (512×512 data points);
   Lateral resolution: 1.56 μm;
   Ultimate vertical resolution: 5 nm.
The roughness parameter can for example be determined using the following:
   Software: WinSAM, Version 2.6.07 (University of Erlangen-Nurnberg)
   Filter: Moving-average Gaussian filter with a cut-off wavelength of x=31 μm, y=30 μm (20×19 image points), subsequent plane subtraction
   KFL-analysis: Limits from the amplitude density, 10 nm increments In addition to the process described above, the present invention further relates to a ceramic body, at least a portion of which has a surface topography that is at least partially formed of a roughness-providing ceramic material.

The surface topography is thereby defined by the arithmetic mean height Sa being in a range from 0.1 μm to 1.7 μm and the roughness-providing ceramic material comprises a calcium containing crystalline phase.

Specifically, the ceramic body comprises a surface region extending from the surface of the body to a predetermined depth and a core region adjoining the surface region in direction to the center of the body. Thereby, the core region is made of a bulk ceramic material and the surface region comprises the roughness-providing ceramic material.

The surface region is typically the outermost region of the body, but does not exclude bodies with a further layer applied onto their surface.

More specifically, the roughness-providing ceramic material in the surface region is integrally formed with the bulk ceramic material in the core region in a continuous material formation. There is, thus, no discrete interface between the bulk ceramic material and the roughness-providing ceramic material.

As a consequence of the process described above comprising a step in which the calcium compound or calcium component is diffused into the basic body, the proportion of calcium in the bulk ceramic material is generally less than in the roughness-providing ceramic material. Consequently, the proportion of calcium in the core region is also generally less than in the surface region.

More specifically, the proportion of calcium in the roughness-providing ceramic material and/or in the surface region increases continuously from the predetermined depth in direction towards the surface of the body. In other words, the proportion of calcium decreases continuously in direction from the surface of the body to the core region. This also includes embodiments of the body, in which the decrease starts from a given depth and having in its outermost region a constant proportion of calcium.

The term "proportion" as used in this context relates to the atomic percentage of calcium relative to the total number of atoms of the ceramic material.

Given the gradual change in the proportion of calcium, also the material properties introduced by the incorporation of calcium changes gradually in direction from the surface of the body to the core region. There are thus no or only unsubstantial strain incompatibilities introduced by the calcium incorporation and the risk of material of the surface region splitting off from the material of the core region is thus relatively low.

More specifically, the calcium containing crystalline phase is solely present in the surface region. Except for the desirable properties originating from the calcium incorporation, the properties of the bulk ceramic material thus remain unaffected.

It is further preferred that the surface region extends from the surface of the body to a depth of at most 10 μm, preferably at most 8 μm (micrometer), more preferably at most 6 μm (micrometer), most preferably at most 5 μm (micrometer).

As mentioned, the ceramic material is preferably made of a ceramic material comprising alumina and/or zirconia, preferably yttria-stabilized zirconia.

As also mentioned, the calcium containing crystalline phase preferably is a Ca—Zr—O phase, more preferably a $CaO$—$ZrO_2$ phase, and even more preferably is selected from the group consisting of a monoclinic $CaZr_4O_9$ phase, a cubic $CaZrO_3$ phase and an orthorhombic $CaZrO_3$ phase. Most preferably, it is an orthorhombic $CaZrO_3$ phase, since the presence of this phase has been shown to go along with a specifically high hydrothermal stability.

For an orthorhombic $CaZrO_3$ phase to be formed, a relatively high amount of calcium or its oxide, respectively, in the surface region is required.

In this regard, it is preferred that the amount of calcium oxide in the surface region preferably ranges from about 3 mol-% to about 50 mol-%, more preferably from about 6 mol-% to about 50 mol-%, and most preferably from about 15 mol-% to about 50 mol-%. In this context, mol-% refers to the number of calcium oxide versus the sum of calcium oxide and zirconia of the material of the surface region.

The $CaO$—$ZrO_2$ crystalline phase can further contain minor amounts of yttrium, hafnium and/or any other stabilizing agent of zirconia, as known to the skilled person. It is understood that these crystalline phases are also encompassed by the terms "Ca—Zr—O phase" and "$CaO$—$ZrO_2$ phase".

It is particularly preferred that in the surface region, the ceramic material comprises a crystalline phase A formed by yttria-stabilized zirconia in tetragonal phase and crystalline phase B formed by the calcium containing crystalline phase, i.e. a phase the crystal structure of which comprising—apart from zirconium and oxygen—calcium in a periodic arrangement, said crystalline phase B having a lower theoretical density than crystalline phase A.

In this regard, it is referred to non-published European patent application No. 12 008 608.7 and 12 008 609.5, the disclosure of which is incorporated herein in their entirety by reference.

Due to the presence of crystalline phase A, the material retains its ability for undergoing martensitic transformation and thus to close cracks and/or to countervail crack propagation in the body.

Due to the formation of crystalline phase B having a lower theoretical density than crystalline phase A, a volume increase with respect to the volume of crystalline phase A is achieved, thus building up a compressive stress within the surface region which ultimately results in an increased flexural strength of the body.

Preferably, the theoretical density of crystalline phase B is also lower than the one of zirconia in monoclinic phase. Thus, even after back-transformation from the monoclinic phase to the tetragonal phase, an increase in the flexural strength of the body can be achieved by the presence of crystalline phase B.

In addition to the increased flexural strength achievable, an improvement in the hydrothermal stability can be achieved, due to the fact that in the surface region at least a portion of the tetragonal phase, which intrinsically has a relatively high tendency for low temperature degradation, is transformed into a phase of higher hydrothermal stability.

Further, it has been shown that by the incorporation of calcium in the surface region also the hydrophilicity of the body's surface can be improved, which is of particular relevance in view of a use of the body as an implant, and more particularly as a dental implant It is understood that all preferred features mentioned for the body of the present invention likewise apply to the process of the present invention and vice versa.

Thus, the ceramic body is preferably made of a ceramic material comprising alumina and/or zirconia, more preferably yttria-stabilized zirconia, as described above;

the calcium containing crystalline phase is preferably a Ca—Zr—O phase, as described above;

the calcium containing crystalline phase is more preferably a CaO—$ZrO_2$ phase, and even more preferably is selected from the group consisting of a monoclinic $CaZr_4O_9$ phase, a cubic $CaZrO_3$ phase and an orthorhombic $CaZrO_3$ phase, and most preferably is an orthorhombic $CaZrO_3$ phase, as described above;

Sa is preferably in a range from 0.3 µm to 0.9 µm, more preferably from 0.4 µm to 0.75 µm, and most preferably from 0.6 µm to 0.75 µm; and the developed surface area Sdr preferably ranges from 5% to 40%, more preferably from 10% to 30%.

As mentioned above, the object achieved by the present invention is particularly useful in the field of implantology, in particular in oral implantology. The present invention thus further relates to the use of the body as an implant, in particular a dental implant. The present invention likewise relates to the use of the body as an abutment.

If the body is used as a dental implant, the portion having the defined surface topography can comprise or be a part of the bone contacting or the soft tissue contacting surface or both.

According to a further aspect, the present invention thus relates to a dental implant, at least the bone contacting region of which having a surface topography that is at least partially formed of a roughness-providing ceramic material, wherein the surface topography is defined by the mean height Sa being in a range from 0.3 µm to 0.9 µm, preferably from 0.4 µm to 0.75 µm, and most preferably from 0.6 µm to 0.75 µm, and the roughness-providing ceramic material comprises a calcium containing crystalline phase.

The process for providing this surface topography preferably comprises the step of roughening the bone tissue contacting region by a subtractive mechanical treatment, in particular sand-blasting, as mentioned above.

According to a still further aspect, the present invention also relates to an abutment or a dental implant, at least the soft tissue contacting region of which having a surface topography, that is at least partially formed of a roughness-providing ceramic material, wherein the surface topography is defined by the mean height Sa being in a range from 0.1 µm to 0.8 µm, preferably from 0.15 µm to 0.5 µm, and the roughness-providing ceramic material comprises a calcium containing crystalline phase.

The process for providing this surface topography of the soft tissue contacting region is typically devoid of any subtractive mechanical treatment step, such as a sand-blasting step.

The present invention is further illustrated by way of the following examples:

EXAMPLES

1. Sample Preparation; First Set 1.1. Blanks

Discs of yttria-stabilized zirconia (Y-TZP) having a polished surface, a thickness of about 2 mm and a diameter of about 14 mm were cleaned with a cleaning solution (Deconex® by Borer Chemie AG, Zuchwil, Switzerland) in a standard cleaning procedure.

1.2. Preparation of Intermediate Body

First, the blanks were subjected to oxygen plasma cleaning.

100 µl of a $CaCO_3$ slurry (having a weight ratio of $CaCO_3$ to $H_2O$ of 1:2) were pipetted onto the surface of the cleaned blanks before drying the samples at 90° C. for 30 minutes.

The dried samples were then subjected to a thermal treatment at 1100° C. for 48 hours.

After the thermal treatment, the samples were cleaned from residual material using a brush, and washed by rinsing with ultrapure water (5 minutes under sonication, then by pivoting ("shaking") for 5 seconds each in two water filled beakers).

The washed samples were then blow-dried under a stream of argon.

1.3. Preparation of the Ceramic Body with the Desired Surface Topography

In order to prepare the ceramic body with the desired surface topography (samples 1.1. to 1.4.), acid treatment of the intermediate body was performed using the following inorganic acids under the following conditions:

Sample 1.1: treatment with concentrated hydrochloric acid (HCl; 32%) in water in a volume ratio of 1:1 at 90° C. for 5 minutes;

Sample 1.2: treatment with concentrated phosphoric acid ($H_3PO_4$; 85%) at 90° C. for 5 minutes;

Sample 1.3: treatment with concentrated phosphoric acid ($H_3PO_4$; 85%) in water in a volume ratio of 1:1 at 90° C. for 10 minutes;

Sample 1.4: treatment with concentrated phosphoric acid ($H_3PO_4$; 85%) in water in a volume ratio of 1:1 at 90° C. for 5 minutes;

Sample 1.5: treatment with concentrated sulphuric acid ($H_2SO_4$; 98%) in water in a water/$H_2SO_4$ volume ratio of 2:1 at 90° C. for 5 minutes.

After the acid treatment, the samples were rinsed with ultrapure water (three times under ultra-sonication for 5 minutes) and then blow-dried with argon.

2. Sample Preparation; Second Set 2.1 Blanks

Discs of yttria-stabilized zirconia (Y-TZP) having a machined surface, a thickness of about 1.5 mm and a diameter of about 5 mm were cleaned with a cleaning solution (Deconex® by Borer Chemie AG, Zuchwil, Switzerland) in a standard cleaning procedure.

The machined discs were sandblasted using corundum with an average grain size from 0.25 mm to 0.5 mm and again subjected to Deconex cleaning.

2.2. Preparation of Intermediate Body

The discs were then subjected to oxygen plasma cleaning.

110 µl of a $CaCO_3$ slurry (having a weight ratio of $CaCO_3$ to $H_2O$ of 1:2) were pipetted onto the surface of the cleaned blanks before drying the samples at 80° C. to 90° C. for 30 minutes.

The dried samples were then subjected to a thermal treatment at 1100° C. for 48 hours.

After the thermal treatment, the samples were cleaned from residual material using a brush, and washed by rinsing with ultrapure water (5 minutes under sonication, then by pivoting ("shaking") for 5 seconds each in two water filled beakers).

The washed samples were then blow-dried under a stream of argon.

2.3. Preparation of the Ceramic Body with the Desired Surface Topography

In order to prepare the ceramic body with the desired surface topography (samples 1.6), acid treatment of the intermediate body was performed using the following inorganic acid under the following conditions:

Sample 1.6: treatment with concentrated sulphuric acid ($H_2SO_4$; 98%) in water in a water/$H_2SO_4$ volume ratio of 3:1 at 90° C. for 5 minutes.

3. Sample Preparation; Third Set 3.1 Blanks

Discs of yttria-stabilized zirconia (Y-TZP) having a machined surface, a thickness of about 1.5 mm and a diameter of about 5 mm were cleaned with a cleaning solution (Deconex® by Borer Chemie AG, Zuchwil, Switzerland) in a standard cleaning procedure.

3.2. Preparation of Intermediate Body

First, the blanks were subjected to oxygen plasma cleaning.

15 µl of a $CaCO_3$ slurry (having a weight ratio of $CaCO_3$ to $H_2O$ of 1:2) were pipetted onto the surface of the cleaned blanks before drying the samples at 80° C. for 15 minutes.

The dried samples were then subjected to a thermal treatment at 1100° C. for 48 hours.

After the thermal treatment, the samples were cleaned from residual material using a brush, and washed by rinsing with ultrapure water (5 minutes under sonication, then by pivoting ("shaking") for 5 seconds each in two water filled beakers).

The washed samples were then blow-dried under a stream of argon.

3.3. Preparation of the Ceramic Body with the Desired Surface Topography

In order to prepare the ceramic body with the desired surface topography (samples 1.7 to 1.8), acid treatment of the intermediate body was performed using hydrofluoric acid (HF) under the following conditions:

Sample 1.7: treatment with concentrated hydrofluoric acid (HF; 40%) in water in a water/HF volume ratio of 4:1 at room temperature for 5 minutes; and Sample 1.8: treatment with concentrated fluoric acid (HF; 40%) in water in a water/HF volume ratio of 80:1 at room temperature for 5 minutes.

The surface topography and the surface composition of samples 1.1, 1.2 and 1.5 as well as of samples 1.7 and 1.8 is shown in the figures, of which FIG. 1 shows scanning electron micrograph (SEM) images of sample 1.1 (A), sample 1.2 (B) and sample 1.5 (C) together with SEM images of the polished blank forming the basic body (D) and of the intermediate body (E) for comparative reasons;

FIG. 2 shows EDX (energy-dispersive X-ray spectroscopy) spectra of sample 1.1 (A), sample 1.2 (B) and sample 1.5 (C) together with EDX spectra of the polished blank forming the basic body (D) and of the intermediate body (E) for comparative reasons; and FIG. 3 shows scanning electron micrograph (SEM) images of sample 1.7 (A) and sample 1.8 (B).

As shown in FIG. 1, the samples obtained by a chemical treatment with HCl, $H_3PO_4$ and $H_2SO_4$ showed a distinctly different surface topography compared to the reference sample, i.e. the polished blank forming the basic body as well as the intermediate body obtained after thermal treatment. Particularly, the sample obtained by $H_3PO_4$ treatment as well as the sample obtained by $H_2SO_4$ treatment showed a clearly increased roughness. In these samples, the grooves originating from the polishing of the surface are no longer visible. In case of the $H_3PO_4$ treatment, an etching structure on the level of grains is achieved, while in case of the $H_2SO_4$ sample cavities in the range of about 1 µm were additionally formed.

Analysis of the samples obtained by different concentrations of $H_3PO_4$ (sample 1.2/1.3 and 1.4) and different treatment times (sample 1.2 and 1.4/1.3) showed that on the level of individual grains, the structures are comparable, but with the mildest conditions (sample 1.4; volume ratio 1:1, treatment duration of 5 minutes) resulting in the lowest overall roughness.

The EDX spectra according to FIG. 2 show that calcium is present for all examples except for the $ZrO_2$ reference sample, but with distinct differences between the samples. The respective amount of Ca, O, Zr and optionally Pd is given in mass-% ("Massen %") in the upper right corner. (Low amounts of Pd or Pt were detected due to the presence of a thin Pt/Pd coating on the sample surface in order to make the surface conductive and thus imagable by the SEM.)

The EDX spectrum of sample 1.1 (HCl) showed only very little calcium, whereas the calcium content of sample 1.2 ($H_3PO_4$) and sample 1.5 ($H_2SO_4$) is comparable to the Ca—$ZrO_2$ reference sample.

Figure 1C:
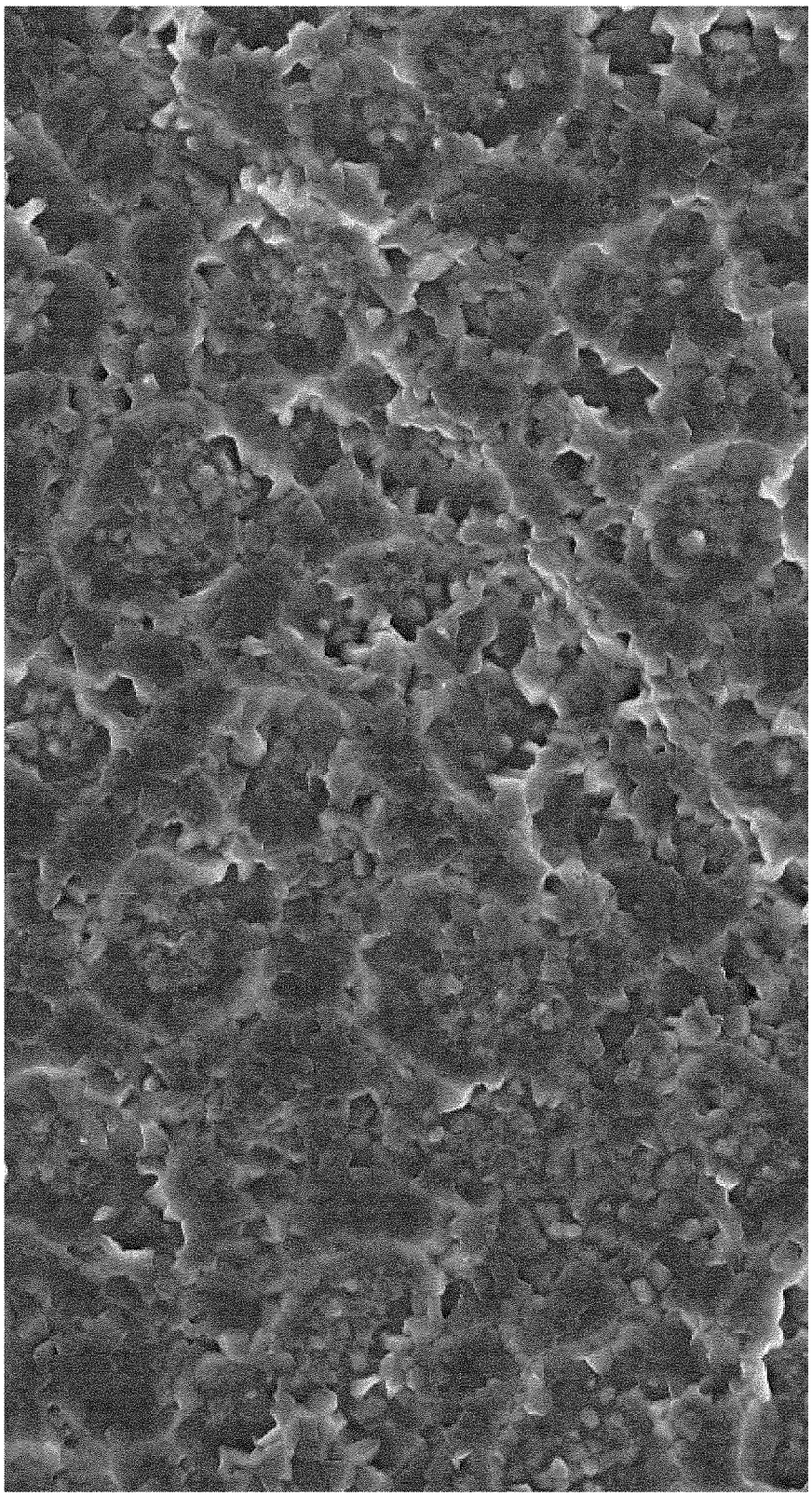
Figure 1D:
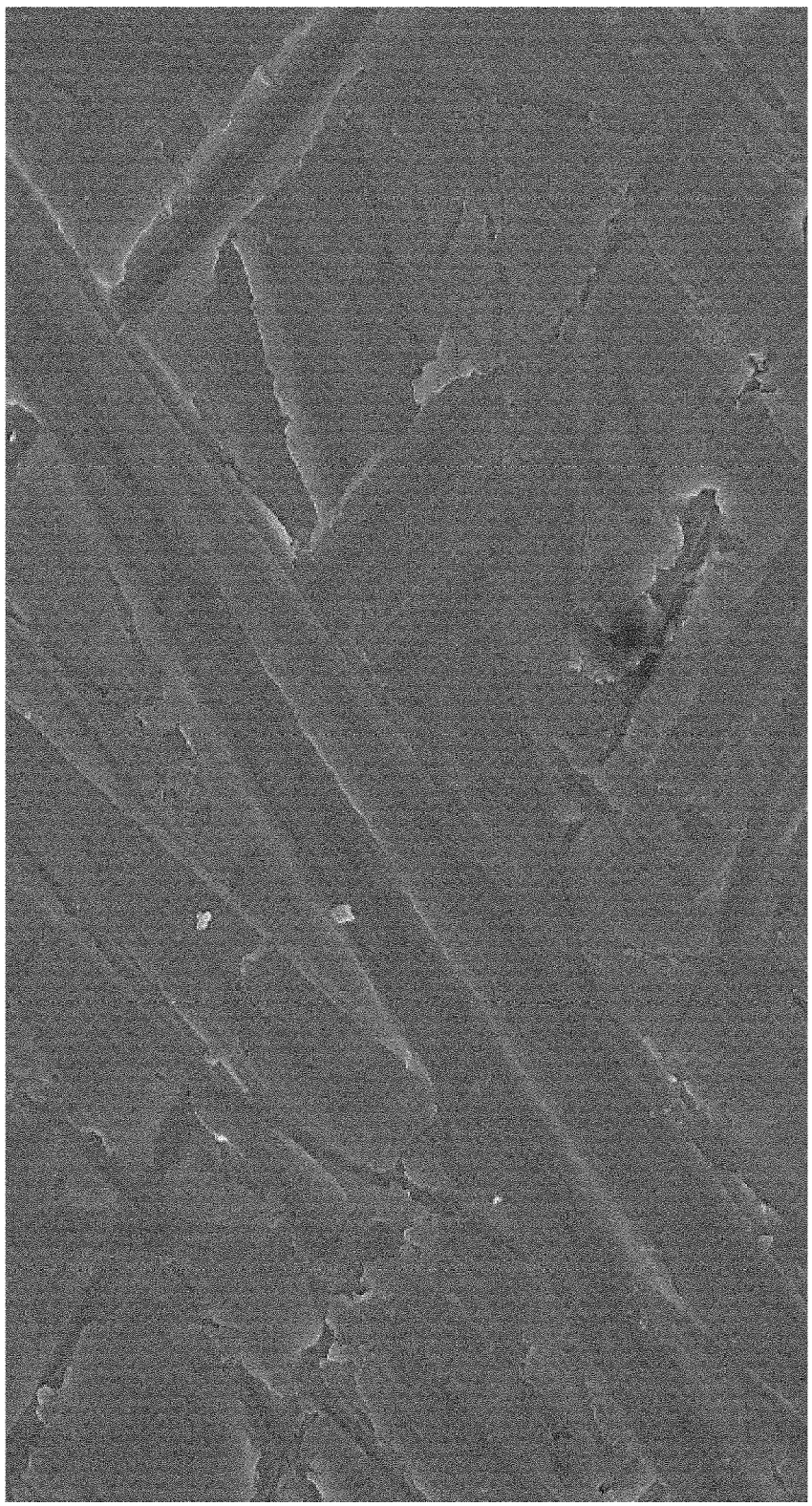
Figure 1E:
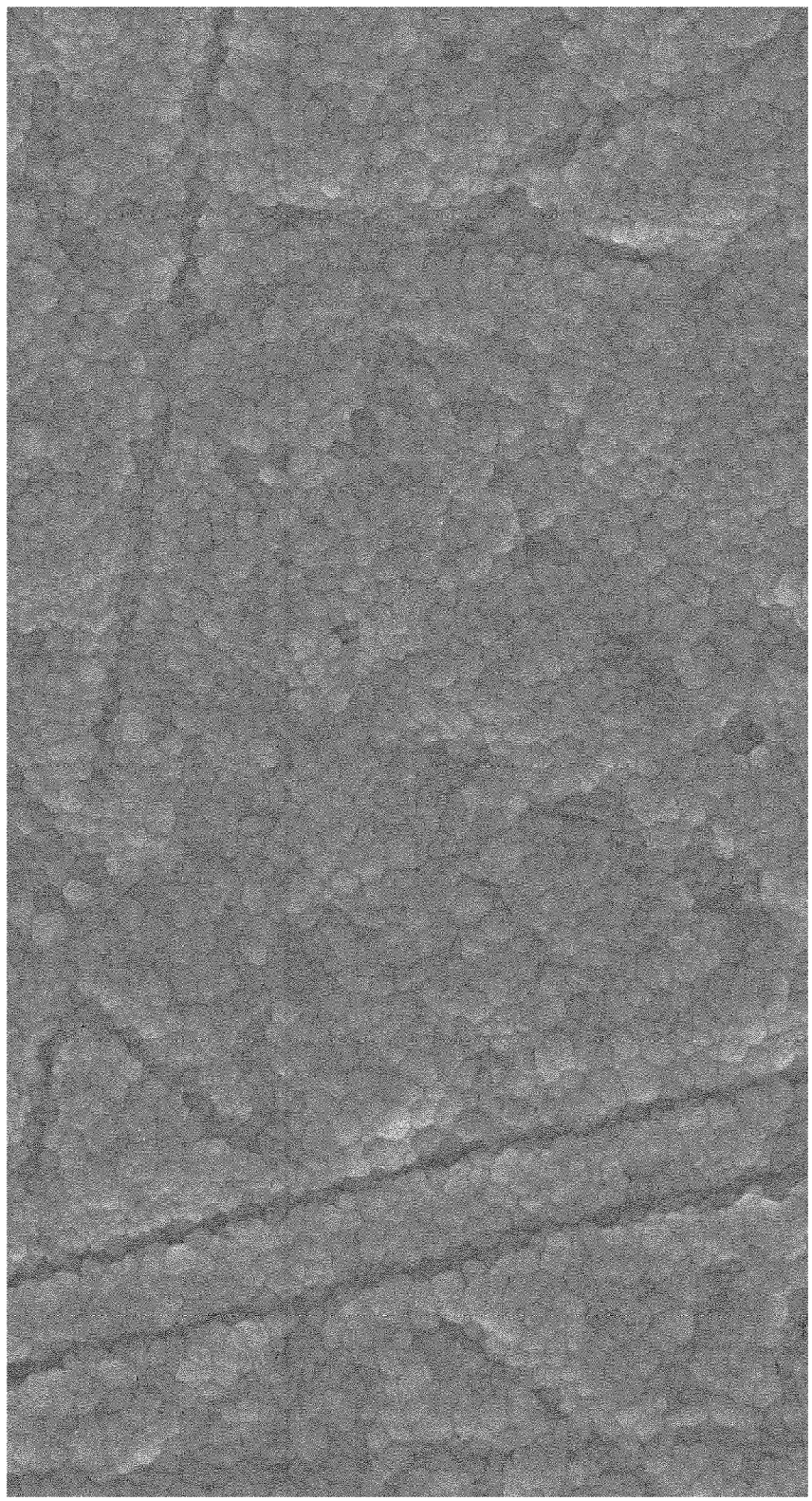
Figure 2A:
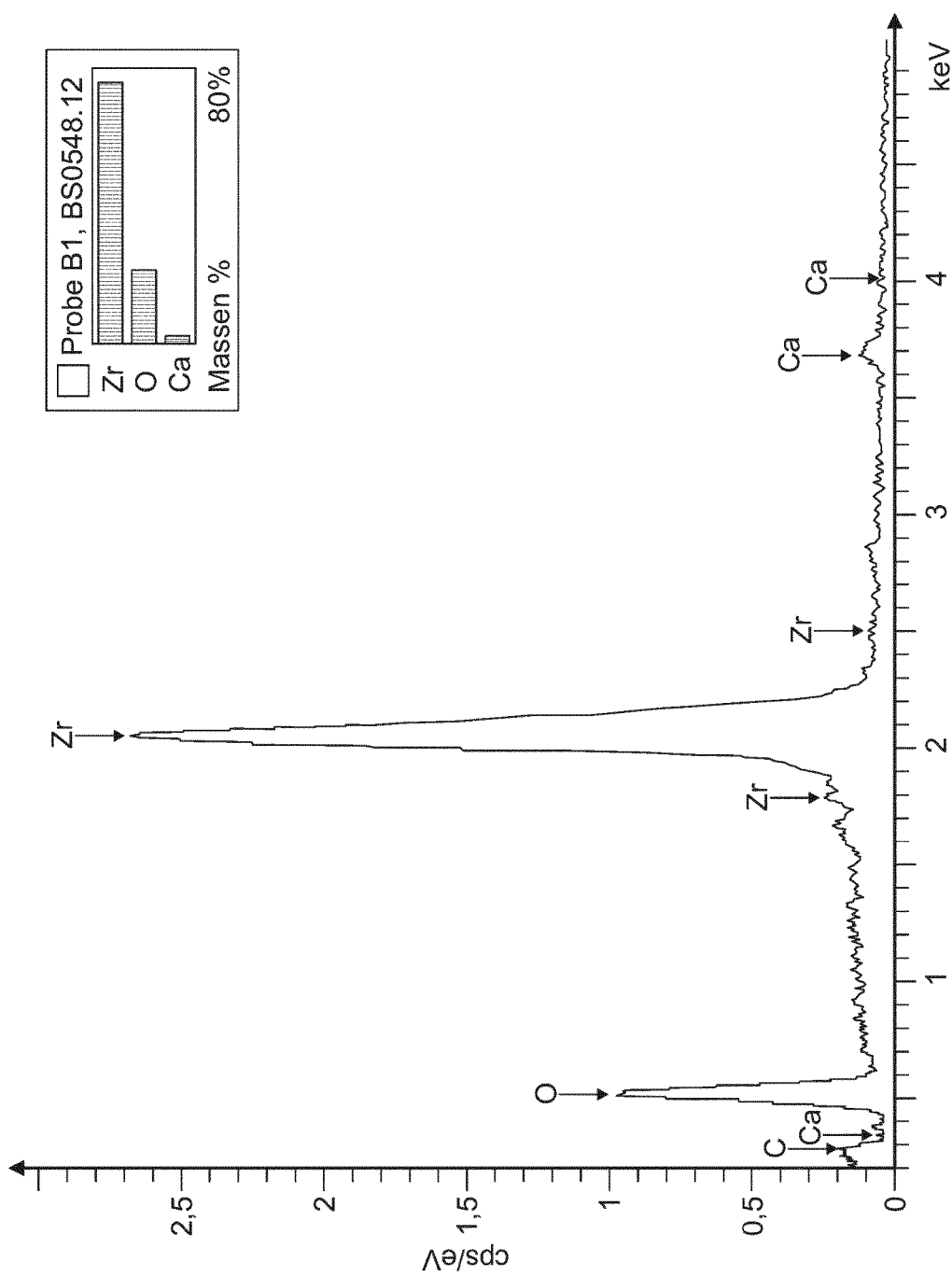
Figure 2B:
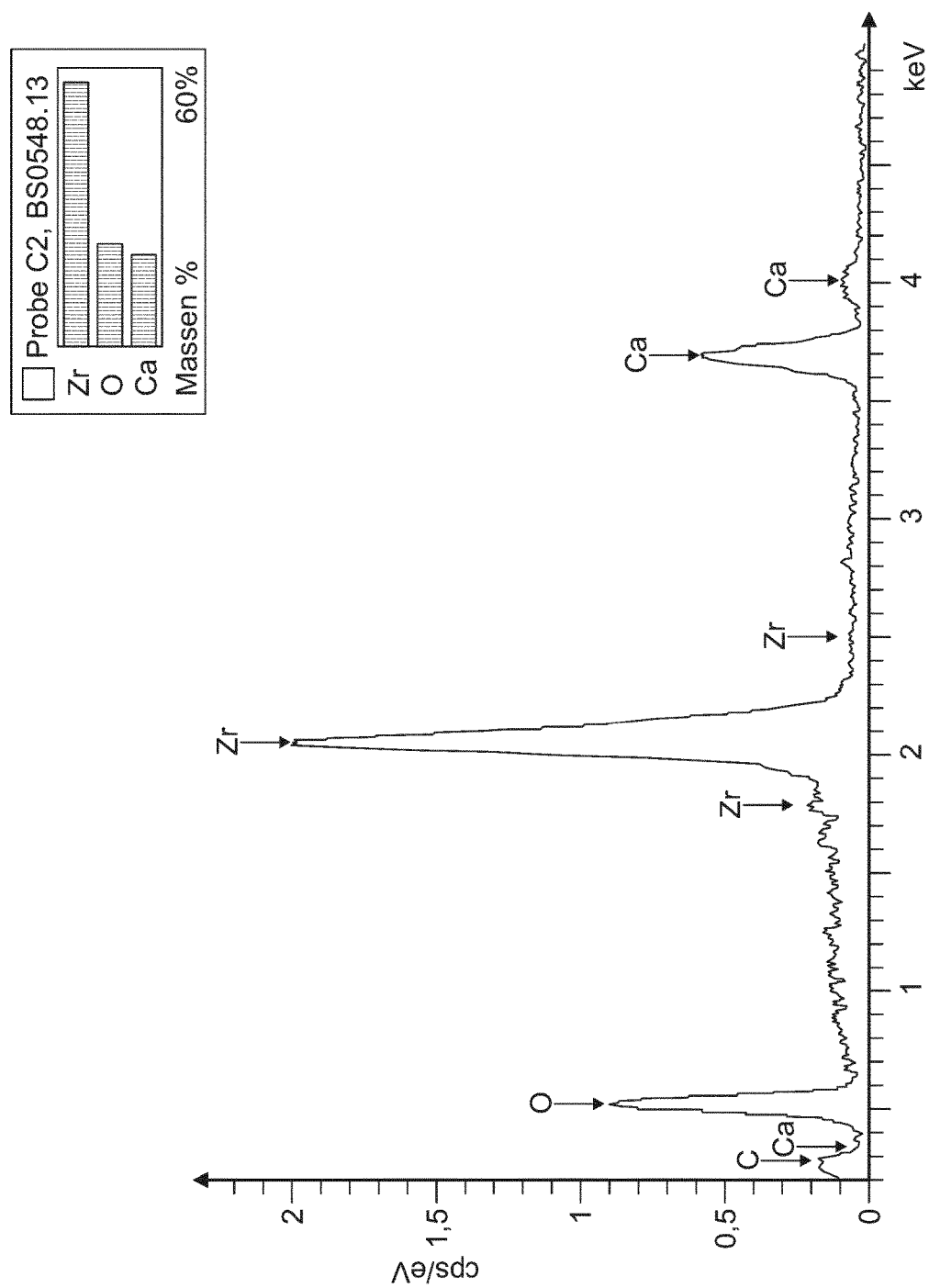
Figure 2C:
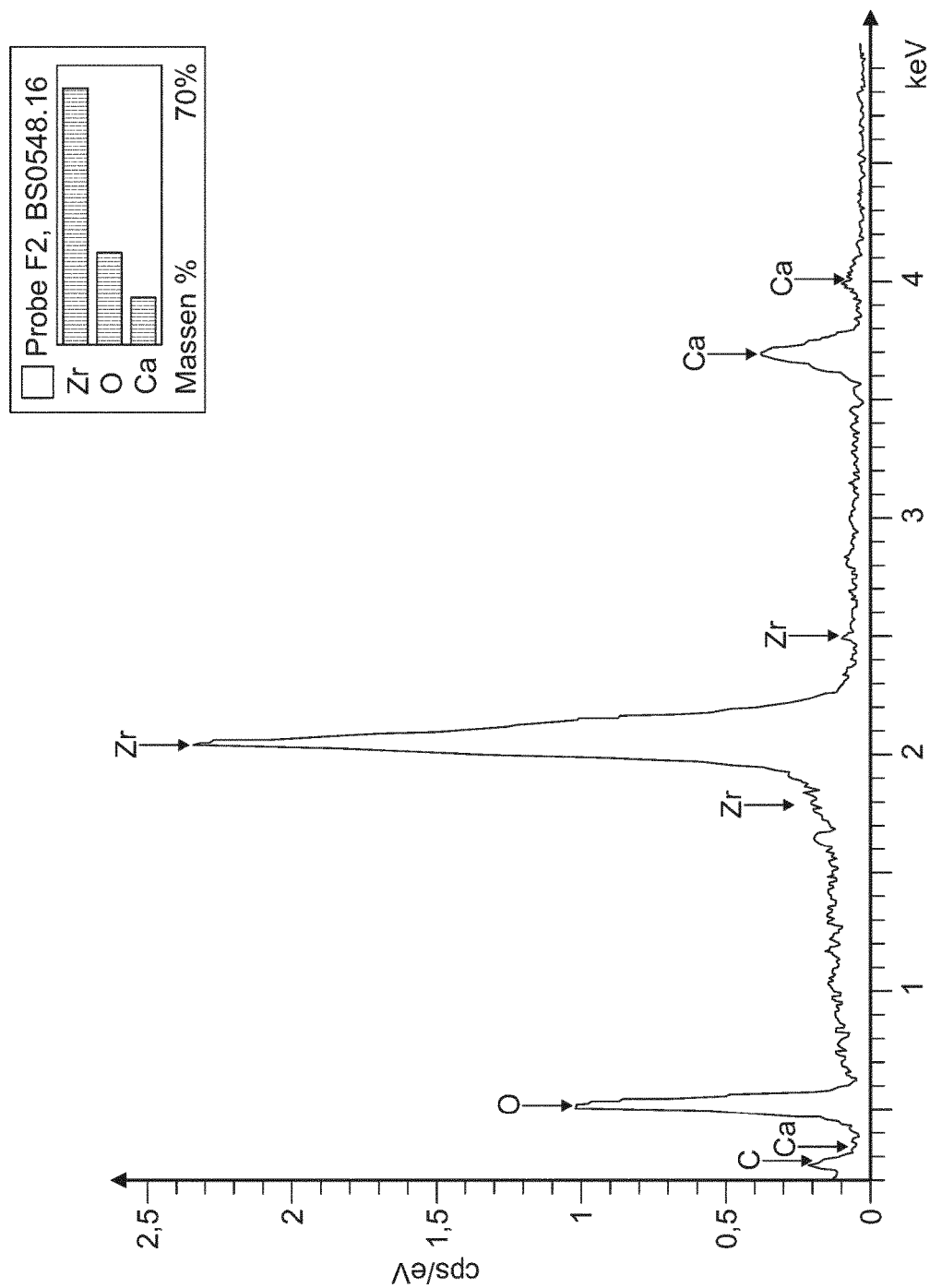
Figure 2D:
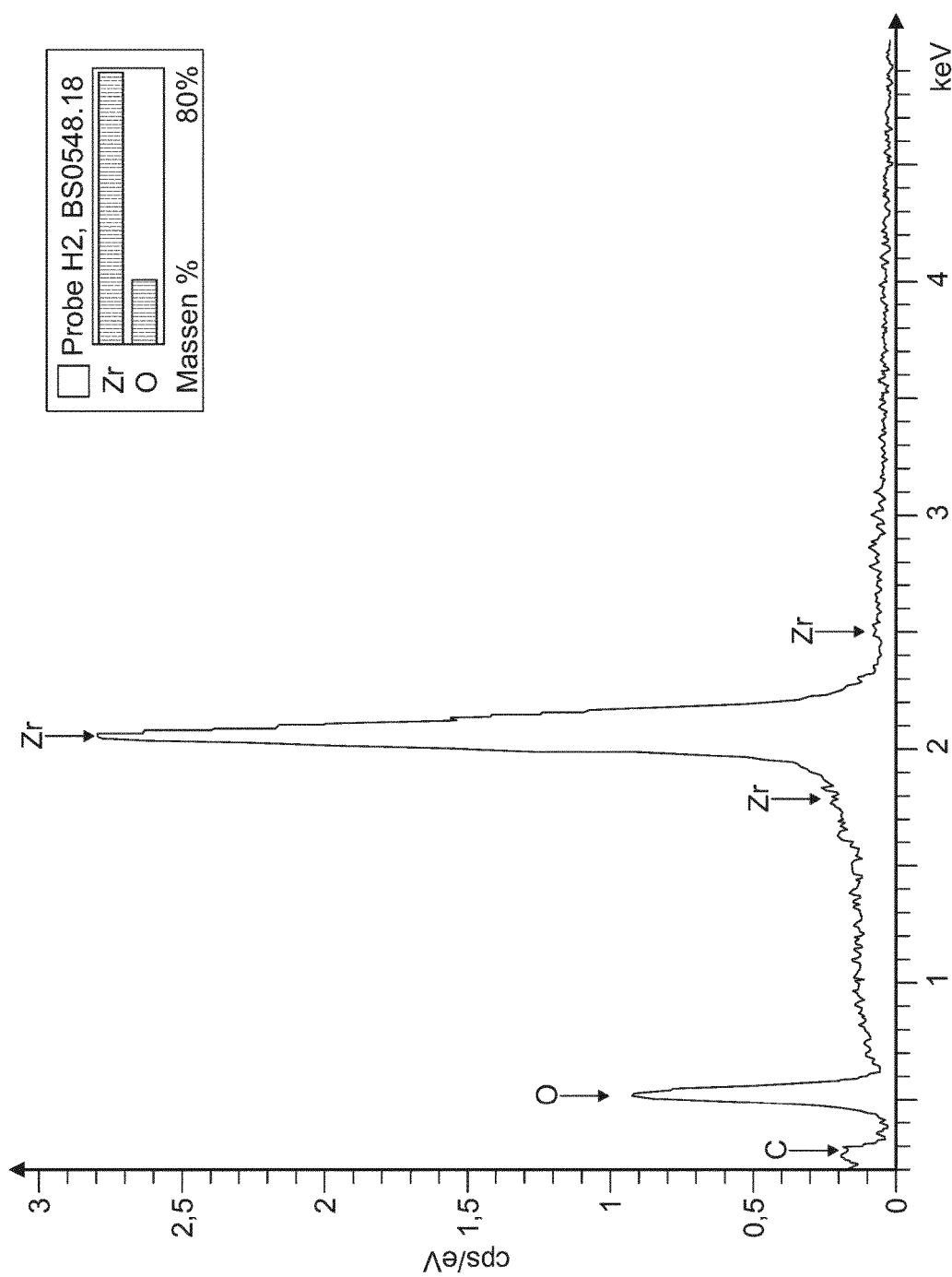
Figure 2E:
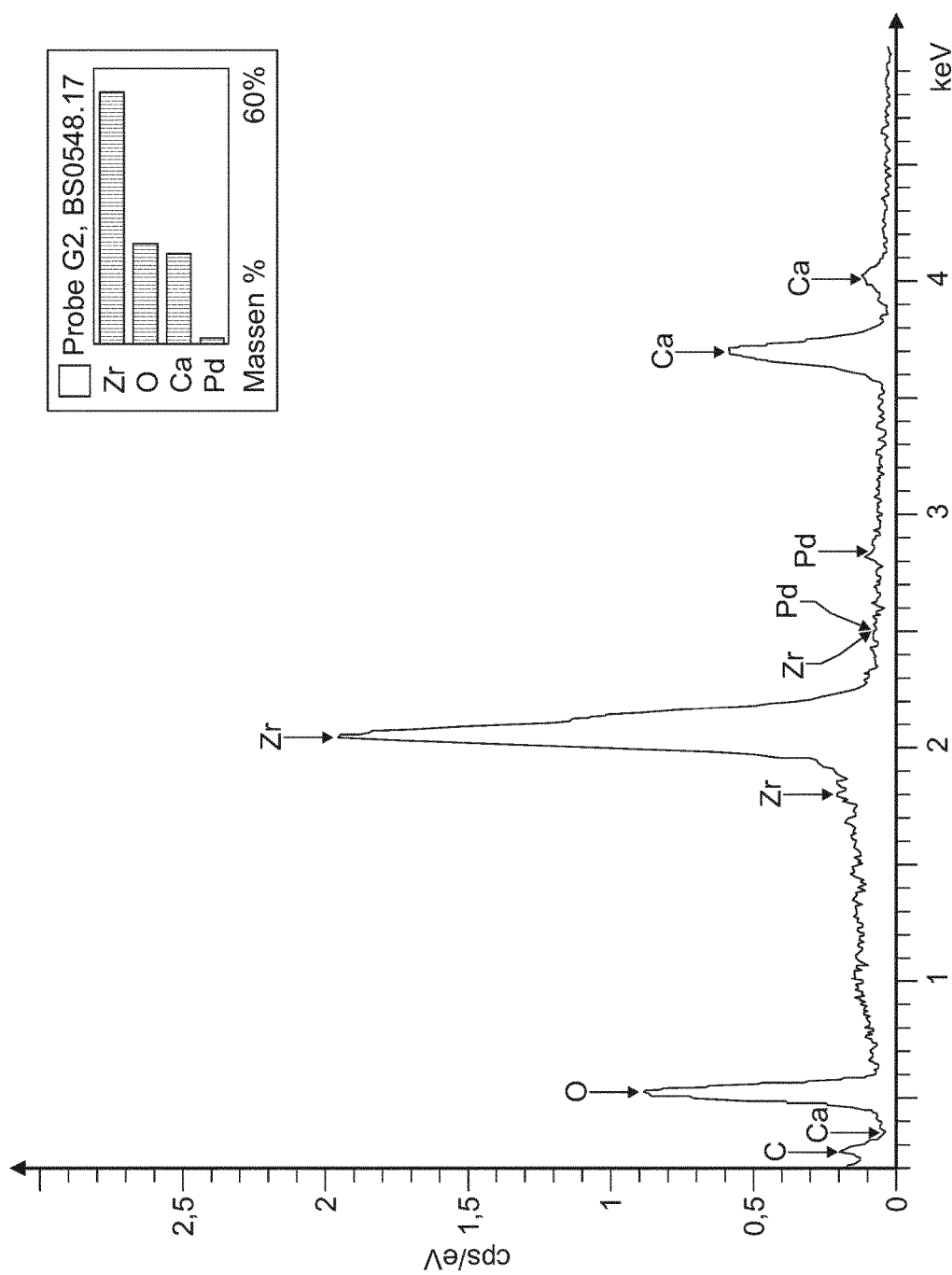

Further tests showed the following in addition to the above findings: In comparison to sample 1.5, the surface topography of which is shown in FIG. 1C, lower concentration of $H_2SO_4$ according to sample 1.6 led to an even more pronounced formation of microstructures as well as nanostructures. Also for sample 1.6, EDX spectra revealed the presence of calcium, indicative of a partial removal of the calcium containing crystalline phase.

The samples obtained by a chemical treatment with HF (samples 1.7 and 1.8) showed the formation of pits having a lateral dimension of about 0.5 µm. This was found both by treatment with HF in a dilution of 1:4 (shown in FIG. 3A) as well as by treatment with HF in a dilution of 1:80 (shown in FIG. 3B). Also for samples 1.7 and 1.8, EDX spectra (not shown) confirmed that the calcium containing crystalline phase was only removed partially.

Figure 3A:
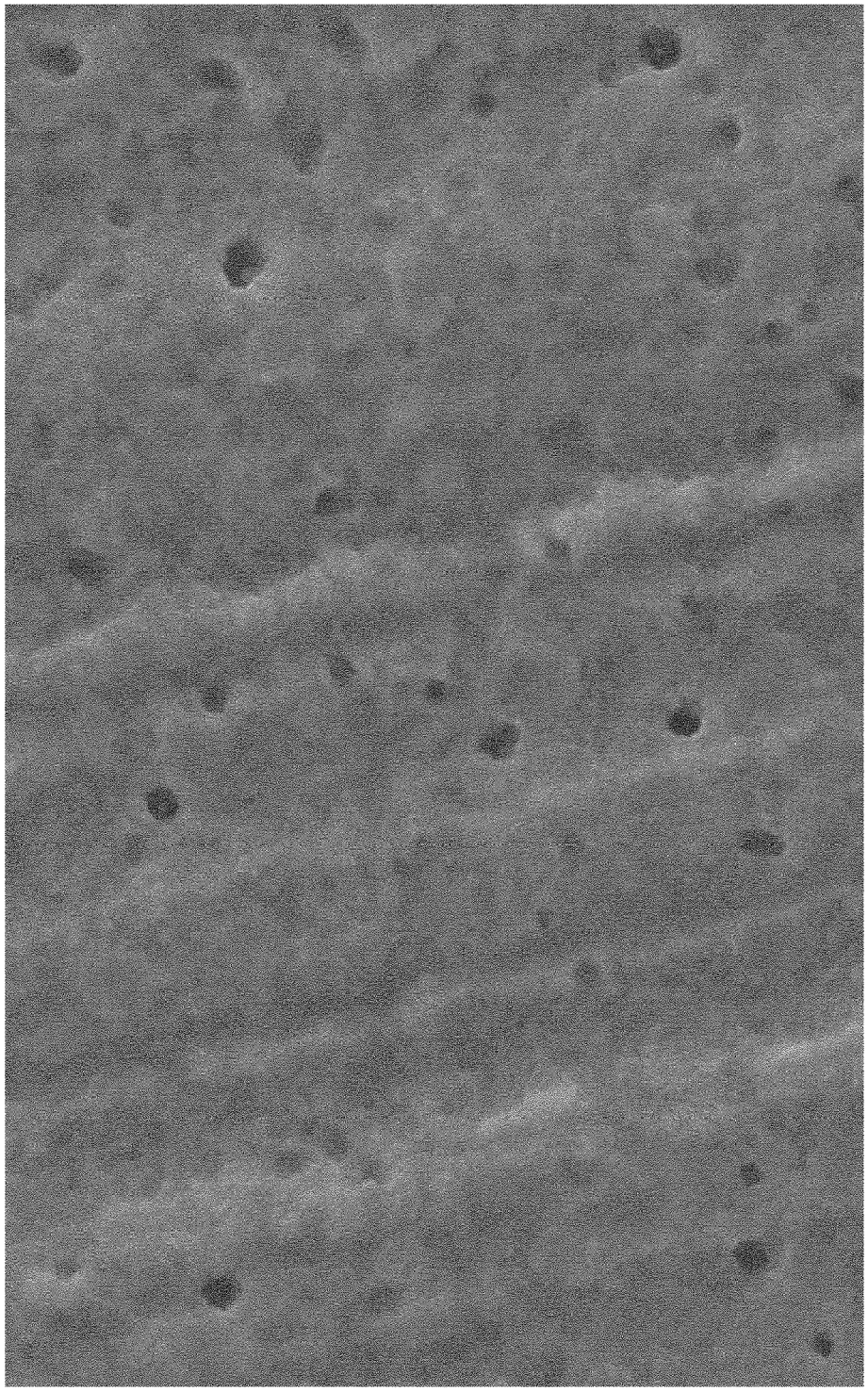
Figure 3B:
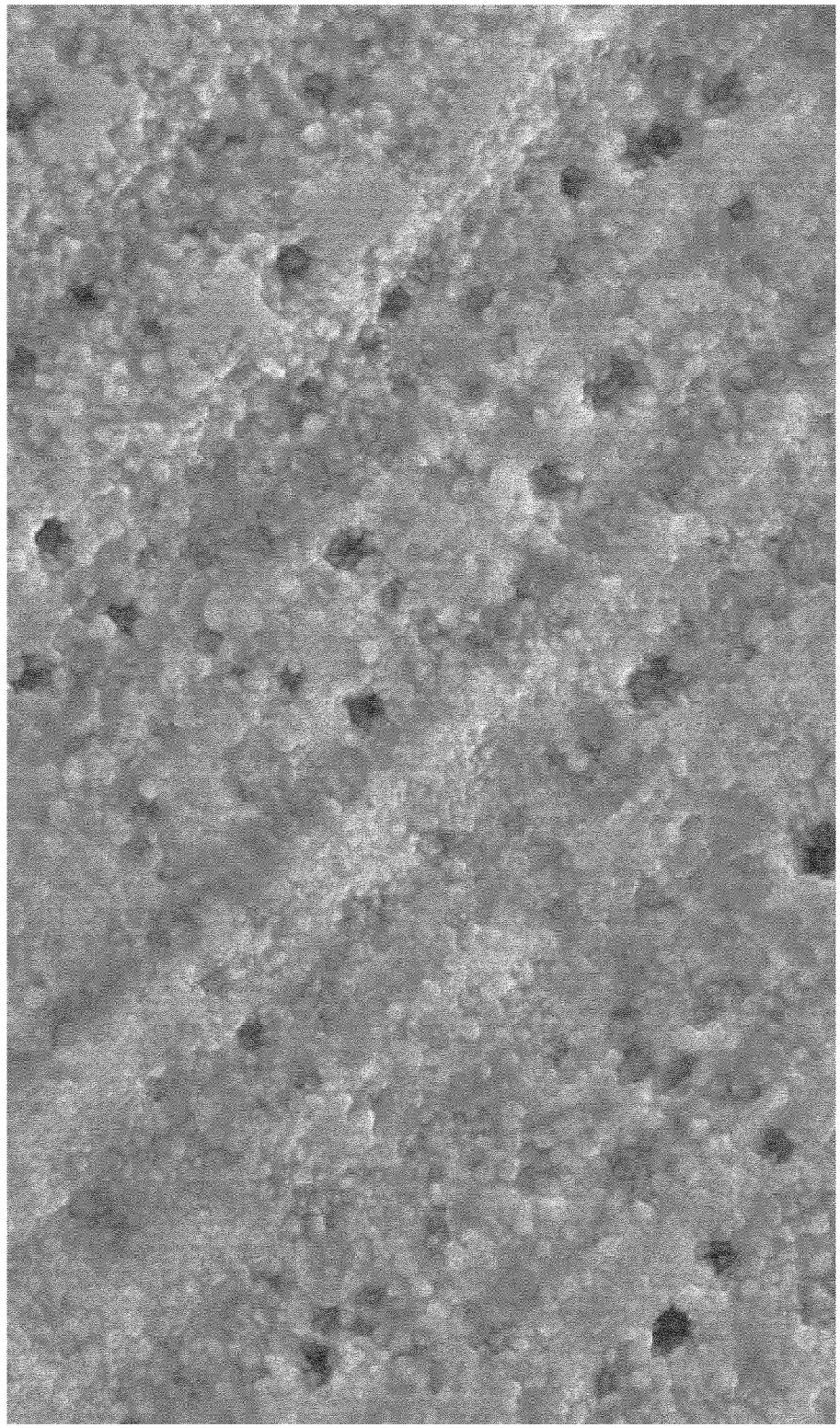

Samples 1.7 and 1.8 thus give clear evidence that a desired surface topography of the ceramic body can be achieved when using highly diluted HF, in particular HF at a concentration low enough to circumvent elaborate safety requirements and further low enough to avoid attack of the yttria-stabilized zirconia. If a more pronounced surface topography than the ones shown in FIGS. 3A and 3B is to be achieved, a longer treatment duration and/or a higher treatment temperature may be chosen.

In summary, the results prove that by the process according to the present invention a rough surface topography is obtained and that the desired roughness can be set by appropriately adjusting the type and concentration of inorganic acid or base as well as by the treatment conditions, in particular the treatment duration and the temperature.

The invention claimed is:

1. Process for providing a defined surface topography to at least a portion of a ceramic body, the process comprising the subsequent steps of
   a) applying a layer of a calcium containing substance comprising at least one calcium compound onto the surface of at least a portion of the ceramic basic body;
   b) thermally treating the ceramic basic body with the layer applied thereon at an elevated temperature, whereby a calcium compound or a calcium component based on the calcium compound diffuses into the basic body to form an intermediate body, said intermediate body comprising in its outermost surface region a calcium containing crystalline phase; and
   c) chemically treating the outermost surface region of the intermediate body with hydrofluoric acid, an inorganic acid other than hydrofluoric acid, or an inorganic base to partially remove the calcium containing crystalline phase, thereby obtaining the surface topography,
   wherein when the hydrofluoric acid is used, it is diluted in water in a volume ratio of water to hydrofluoric acid of at least 4:1.

2. Process according to claim 1, wherein the ceramic basic body is made of a ceramic material comprising alumina and/or zirconia.

3. Process according to claim 1, wherein the calcium containing crystalline phase is a Ca—Zr—O phase.

4. Process according to claim 3, wherein the calcium containing crystalline phase is a $CaO$—$ZrO_2$ phase.

5. Process according to claim 1, wherein the calcium compound contained in the calcium containing substance is selected from the group consisting of a calcium salt, calcium oxide, calcium hydroxide, metallic calcium, and mixtures thereof.

6. Process according to claim 1, wherein the thermal treatment of step b) is carried out at a temperature of at least 500° C.

7. Process according to claim 1, wherein an inorganic acid selected from the group consisting of $HNO_3$, HCl, HF diluted in water in a volume ratio of water to hydrofluoric acid of at least 4:1, $H_3PO_4$ and $H_2SO_4$ and mixtures thereof, is used for the chemical treatment of step c).

8. Process according to claim 1, further comprising a step of roughening at least a part of the surface of the basic body by a subtractive mechanical treatment.

9. Process according to claim 1, wherein the surface topography is defined by the arithmetic mean height Sa being in a range from 0.1 μm and 1.7 μm.

10. Process according to claim 1, wherein the surface topography is further defined by a developed surface area Sdr being in a range from 5% to 40%.

11. Process according to claim 1, wherein step c) is carried out with an inorganic acid other than hydrofluoric acid.

12. Process according to claim 1, wherein step c) is carried out with hydrofluoric acid diluted in water in a volume ratio of water to hydrofluoric acid of at least 80:1.

* * * * *